United States Patent [19]

Jubin et al.

[11] 4,080,387
[45] Mar. 21, 1978

[54] PROCESS FOR CONCENTRATION OF CYCLOHEXANE OXIDATE

[75] Inventors: John Chester Jubin, Wallingford; Isadore Edward Katz, Springfield; Richard Gilbert Tave, Broomall, all of Pa.

[73] Assignee: Atlantic Richfield Company, Los Angeles, Calif.

[21] Appl. No.: 725,753

[22] Filed: Sep. 23, 1976

[51] Int. Cl.$^2$ ............................................. C07C 179/08
[52] U.S. Cl. .............................. 260/610 A; 260/610 B
[58] Field of Search ............ 260/610 A, 610 B, 610 R

[56] References Cited

U.S. PATENT DOCUMENTS

| 2,383,919 | 8/1945 | Rust | 203/55 |
|---|---|---|---|
| 2,931,834 | 4/1960 | Cruch et al. | 260/586 |
| 3,480,519 | 11/1969 | Baker, III et al. | 203/55 |
| 3,949,003 | 4/1976 | Zajacek et al. | 260/610 |
| 3,949,004 | 3/1976 | Sorgenti et al. | 260/610 |

FOREIGN PATENT DOCUMENTS

| 700,546 | 12/1953 | United Kingdom | 260/610 |

Primary Examiner—James O. Thomas, Jr.
Assistant Examiner—Werren B. Lone
Attorney, Agent, or Firm—John R. Ewbank

[57] ABSTRACT

A cyclohexane oxidate containing from about 2% to about 12% cyclohexyl hydroperoxide is modified by the addition of tertiary butyl alcohol. A feedstock containing the cyclohexane oxidate and from about 13% to about 67% tertiary butyl alcohol is directed to a vacuum distillation zone. An azeotrope of tertiary butyl alcohol and cyclohexane is recovered as distillate in the vacuum distillation zone, providing a bottoms fraction containing cyclohexyl hydroperoxide in a greater concentration than in he feedstock. Such CHHP concentration in the bottoms may be in a range from about 10% to about 30%. Cyclohexyl hydroperoxide can decompose to form products including cyclohexanol and cyclohexanone and this or other decompositions occur more rapidly at the elevated temperatures of any distillation, thus hampering efforts at concentration of CHHP. By using TBA as an azeotroping agent, the CHHP is satisfactorily concentrated with an advantageously small amount of decomposition of CHHP.

1 Claim, No Drawings

PROCESS FOR CONCENTRATION OF CYCLOHEXANE OXIDATE

FIELD OF INVENTION

This invention relates to the preparation of relatively concentrated solutions of cyclohexyl hydroperoxide, to the methods for concentrating cyclohexyl hydroperoxide, and to the azeotropic distillation of compositions containing CHHP.

PRIOR ART

Sheng et al U.S. Pat. No. 3,862,961 employs a molybdenum containing catalyst and tertiary butyl alcohol as a co-solvent for a hydroperoxide in oxidizing propylene to propylene oxide.

Crouch et al U.S. Pat. No. 2,931,834 describes the preparation of cyclohexanol by an oxidation of cyclohexane followed by concentration of the oxidate by normal distillation.

Bonnart et al U.S. Pat. No. 3,510,526 oxidizes a mixture of fresh plus recycled cyclohexane in order to prepare cyclohexyl hydroperoxide. The recycled cyclohexane is subjected to mild caustic extraction.

In the production of useful products such as propylene oxide, it is advantageous for the hydroperoxide to be of a concentration of a magnitude of 20%. However, the oxidation of cyclohexane to form cyclohexyl hydroperoxide is conveniently regulated to produce cyclohexyl hydroperoxide in a concentration of the magnitude from about 2% to about 12%. Accordingly, there has been a long standing need for appropriate procedures for the concentration of the cyclohexyl hydroperoxide. A large market exists for nylon, caprolactam, adipic acid, phenol, cyclohexanone, cyclohexanol, and related derivatives from the coproducts resulting from using CHHP to make propylene oxide. Notwithstanding this long standing need and notwithstanding the attractiveness of cyclohexyl hydroperoxide for the production of propylene oxide, prior art technologists have been frustrated in attempts at providing an attractive procedure for the concentration of cyclohexyl hydroperoxide.

SUMMARY OF INVENTION

In accordance with the present invention, a feedstock stream to a vacuum distillation zone consists of a mixture of cyclohexane oxidate and tertiary butyl alcohol. The temperature and pressure of the vacuum distillation are so controlled that the distillate is an azeotrope of cyclohexane and tertiary butyl alcohol. The increase in the concentration of the cyclohexyl hydroperoxide is achieved by azeotropic vacuum distillation at a temperature and at conditions minimizing the decomposition of the cyclohexyl hydroperoxide. After the cyclohexane has been converted to products comprising CHHP, the cyclohexane oxidate is transferred to an adjustment zone in which the concentration of TBA (i.e. tertiary butyl alcohol) is regulated to provide an amount sufficient to permit the satisfactory operation of the subsequent vacuum distillation step.

The invention is further clarified by reference to a plurality of examples.

EXAMPLE 1

Cyclohexane was oxidized to form a mixture containing about 6% cyclohexyl hydroperoxide, about 0.9% cyclohexanone and about 1.2% cyclohexanol plus about 3.6% of miscellaneous materials. The cyclohexane oxidate was transferred to a modification zone in which the amount of added TBA (tertiary butyl alcohol) corresponded to about 36.6% of the composition or about 66% of the weight of the cyclohexane. The mixture of cyclohexane and TBA had the proportions of a solvent mixture of about 60.4% cyclohexane and about 39.6% TBA. This feedstock, comprising such solvent and the oxidized components, was advanced to a distillation zone.

This distillation zone was established to permit the vacuum distillation of a distillate constituting essentially an azeotropic mixture of about 70% cyclohexane and about 30% tertiary butyl alcohol. The batch was transferred to the distillation kettle and heated gradually to promote the azeotropic vacuum distillation of the cyclohexane and tertiary butyl alcohol. The distillation column had an inside diameter of about 2 inches and had about 10 theoretical plates. The vacuum was maintained so that the pressure was about 100 millimeters of mercury corresponding to about 0.13 atmosphere or about 1.93 psia. The kettle temperature was maintained near 40° to 48° and was gradually raised to maintain an appropriate rate of distillate formation. The distillation under vacuum was continued for about 11 hours. The reflux ratio was about 0.5 to 1 during much of the distillation. The results of the distillation are summarized in Table 1.

TABLE 1

| | Oxidate & TBA Diluent | | Distillate | | Bottoms | |
|---|---|---|---|---|---|---|
| | Gms. | Wt. % | Gms. | Wt. % | Gms. | Wt. % |
| Cyclohexane (CH) | 7569 | 55.6 | 7128 | 70.4 | 16 | 0.7 |
| T-Butyl Alcohol (TBA) | 4979 | 36.6 | 2908 | 28.7 | 1314 | 58.2 |
| Cyclohexyl Hydroperoxide (CHHP) | 548 | 4.0 | | | 553 | 24.5 |
| Cyclohexanone ($C_6H_{10}O$) | 82 | 0.6 | | | 51 | 2.3 |
| Cyclohexanol ($C_6H_{11}OH$) | 106 | 0.8 | | | 77 | 3.4 |
| Miscellaneous | 336 | 2.4 | 89 | 0.9 | 248 | 10.9 |
| TOTAL | 13620 | 100.0 | 10125 | 100.0 | 2259 | 100.0 |

Attention is called to the fact that the bottoms fraction has an amount of cyclohexyl hydroperoxide corresponding essentially to that of the feedstock, but that substantially all of the cyclohexane has been transferred to the distillate. The concentration of the CHHP in the bottoms is of the general magnitude of 25%, and thus suitable for use in further steps such as the production of propylene oxide. The distillate consists essentially of a wet azeotropic mixture of cyclohexane and TBA. Some of the miscellaneous compounds are volatilized into such azeotrope. The data indicate that the azeotropic distillation of TBA and CH retaining excess TBA in the bottoms permits the concentration of the CHHP from about 4% to about 25% without significant destruction of the thermally sensitive CHHP.

The results from the preparation of a cyclohexane oxidate in the presence of a minor amount of tertiary butyl alcohol were evaluated in Control A. The desired oxidation to cyclohexyl hydroperoxide is promoted by the presence of a minor amount of tertiary butyl alcohol. However, no additional tertiary butyl alcohol is added after formation of the cyclohexane oxidate and prior to the azeotropic distillation of Control A. In such control the cyclohexane oxidate was distilled without adding any more TBA than was used in the oxidation step. In this control, the cyclohexane oxidate was distilled at 115 millimeters pressure and at a temperature within a range from about 35° C to about 47° C. The reflux ratio was maintained at 1 to 1 for 92% of the distillate, and was maintained at 5 to 1 during the collection of the last 8% of the distillate. Data relating to the distillation are shown in Table 2.

TABLE 2

|  | Feed | | Bottoms | | Distillate | |
| --- | --- | --- | --- | --- | --- | --- |
|  | g | Wt % | g | Wt % | g | Wt % |
| Cyclohexane | 285.32 | 86.20 | 14.56 | 50.20 | 257.2 | 90.1 |
| Tertiary Butyl Alcohol | 28.90 | 8.73 | | | 27.4 | 9.60 |
| Cyclohexyl Hydroperoxide | 11.25 | 3.40 | 9.12 | 31.44 | | |
| Cyclohexanone | 3.34 | 1.01 | 1.52 | 5.24 | | |
| Cyclohexanol | | | 2.52 | 8.70 | | |
| Acids | 1.04 | 0.31 | 0.91 | 3.14 | | |
| H₂O | 0.77 | 0.23 | | | 0.77 | 0.27 |
| Residue | 0.37 | 0.11 | 0.37 | 1.28 | | |
| | 331.00 | 99.99 | 29.0 | 100.00 | 286.9 | 99.97 |

It should be noted that the cyclohexyl hydroperoxide recovered is about 19% less than in the feed; partly because some cyclohexyl hydroperoxide is converted to undesired byproducts such as acids, cyclohexanol and cyclohexanone by the distillation. Such 19% loss of CHHP is a serious deficiency of Control A. It should be noted that there would be need for cyclohexyl hydroperoxide production facilities approximately 25% larger if the distillation were conducted in accordance with Table 2 instead of Table 1. Thus the azeotropic distillation has advantages in the preparation of relatively concentrated solutions of CHHP such as are used in the co-production of propylene oxide and a mixture of cyclohexanol and cyclohexane. The amount of tertiary butyl alcohol employed in Control A is well below the 13% tertiary butyl alcohol identified as the minimum for achieving the advantageous quantities of azeotropic distillate and residual TBA in the bottoms required by the present invention. Because Control A indicated that the vacuum distillation of the cyclohexane from the cyclohexane oxidate led to the decomposition of an excessive amount of cyclohexyl hydroperoxide, the control is deemed to establish the requirement for regulating the azeotropic distillation so that the distillation is consistently an azeotrope of cyclohexane and tertiary butyl alcohol throughout the entire vacuum distillation operation, such regulation being the inclusion of adequate TBA in the feedstock, or the periodic addition of TBA for maintaining the desired azeotropic distillation and residual TBA in the distillation bottoms.

EXAMPLE 2

Cyclohexane is subjected to a gas stream containing about 10% oxygen at a pressure of about 17 atmosphere at about 160° C for several hours to produce a cyclohexane oxidate. Such oxidate is transferred to a modification zone in which tertiary butyl alcohol is added so that the TBA represents slightly less than 27% of the mixture. Such mixture is directed as a feedstock to a distillation zone having two fractional distillation columns. Data relating to the distillation are set forth in Table 3. From the bottom of the second column of the two column vacuum distillation system, a stream is withdrawn consisting of cyclohexyl hydroperoxide in tertiary butyl alcohol, the concentration of the CHHP in the TBA being about 19%, which solution is suitable for transfer to a zone for the oxidation of propylene. Data relating to the distillation are set forth in Table 3.

The dilute oxidate is fed to the middle of the first distillation tower, the bottoms of which are fed to the second distillation tower. The concentrated oxidate is withdrawn from the bottom of the second tower. Tertiary butyl alcohol diluent is added in the second tower to supplement the TBA added in the modifying zone prior to the introduction of the feedstock to the first tower. Various schemes for recycling components are possible using a distillative concentration approach of the type shown in Table 3.

TABLE 3

| | Compositions in Primary - Column | | | | | |
| --- | --- | --- | --- | --- | --- | --- |
| | First Feed | | Bottoms | | Distillate | |
| | Moles/hr | Mole % | Moles/hr | Mole % | Moles/hr | Mole % |
| TBA | 6287.10 | 26.81 | 811.42 | 20.00 | 5475.68 | 28.23 |
| ANE | 15387.40 | 65.61 | 2004.46 | 49.40 | 13382.94 | 69.00 |
| OL | 146.75 | 0.63 | 146.75 | 3.62 | 0 | 0 |
| ONE | 81.07 | 0.35 | 79.61 | 1.96 | 1.46 | 0.01 |
| CHHP | 817.80 | 3.49 | 817.80 | 20.16 | 0 | 0 |
| Water | 533.33 | 2.27 | 3.12 | 0.08 | 530.21 | 2.73 |
| Misc. | 199.33 | 0.86 | 194.19 | 4.79 | 5.14 | 0.03 |
| TOTAL | 23452.78 | 100.02 | 4057.35 | 100.01 | 19395.43 | 100.0 |
| | | | 75° C | 616 mm | 46° C | 518 mm |

| | Compositions in Secondary - Column | | | | | | | |
| --- | --- | --- | --- | --- | --- | --- | --- | --- |
| | First Feed | | Second Feed | | Bottoms | | Distillate | |
| | Moles/hr | Mole % | Moles/hr | Mole % | Moles/hr | Mole % | Moles/hr | Mole % |
| TBA | 811.42 | 20.00 | 3098.00 | 100 | 3097.94 | 71.45 | 811.48 | 28.78 |
| ANE | 2004.46 | 49.40 | | | 0.73 | 0.02 | 2003.73 | 71.08 |
| OL | 146.75 | 3.62 | | | 146.75 | 3.38 | 0 | 0 |
| ONE | 79.61 | 1.96 | | | 79.48 | 1.83 | 0.13 | 0.01 |
| CHHP | 817.80 | 20.16 | | | 817.79 | 18.86 | 0.01 | 0 |
| Water | 3.12 | 0.08 | | | 0.01 | 0 | 3.11 | 0.11 |
| Misc. | 194.19 | 4.79 | | | 193.45 | 4.46 | 0.74 | 0.03 |
| TOTAL | 4057.35 | 100.01 | 3098.00 | 100.0 | 4336.15 | 100.0 | 2819.20 | 100.01 |
| | 75° C | | 82° C | | 81° C | 567 mm | 43° C | 412 mm |

EXAMPLE 3

A mixture of cyclohexane and tertiary butyl alcohol corresponding essentially to the mixture of the distillates from the primary column and second column of Example 2 and consisting of a mixture of about 29% tertiary butyl alcohol and about 71% cyclohexane is dried, (using a sorptive type of dryer) to remove the water formed in the previous oxidation step. The thus dried mixture of cyclohexane and tertiary butyl alcohol is directed to a pressurized oxidation reactor as a recycle stream. Fresh cyclohexane is introduced into the reactor in an amount corresponding essentially to that converted into the contemplated products, i.e. cyclohexyl hydroperoxide, cyclohexanone, cyclohexanol and miscellaneous materials. A gas mixture consisting of 8% oxygen and about 2% argon and about 90% nitrogen is directed through the reactor at about 17 atmospheres pressure at about 160° C provide a cyclohexane oxidate corresponding essentially to the first feed of Example 2. The secondary column is operated differently from Example 2 in that no additional tertiary butyl alcohol is injected and the bottoms fraction contains a significant amount of cyclohexane as well as a smaller proportion of tertiary butyl alcohol. The bottom fraction from the secondary column is suitable for directing to an epoxidation zone used for the preparation of propylene oxide from propylene. By this process the cyclohexane is oxidized to cyclohexyl hydroperoxide and is thereafter concentrated into a stream suitable for efficient utilization in the propylene oxide formation step.

EXAMPLE 4

Cyclohexane was oxidized to form a mixture comprising about 3% cyclohexyl hydroperoxide and the cyclohexane oxidate was directed to a modification zone. The amount of tertiary butyl alcohol added in the modification zone was essentially equal to that of the cyclohexane content of the oxidate. The thus modified mixture was directed as a feedstock to a vacuum distillation zone and subjected to two stages of azeotropic distillation on a continuous basis to provide distillate consisting of cyclohexane, tertiary butyl alcohol and water and to provide a bottoms fraction suitable for use in the reaction with propylene to prepare propylene oxide. The distillate was separated to provide a purified cyclohexane fraction for recycle to the oxidation reactor and a TBA fraction suitable for recycling to the modification zone.

By a series of tests, it is established that the oxidation of the cyclohexane must occur in the liquid phase using an oxygen containing gas. Such oxidizing gas should contain from about 4% to about 30% oxygen and desirably about 4% to about 16% oxygen. The oxidizing gas is generally injected into the liquid reaction mixture near the bottom of the reactor, and the effluent gas stream is withdrawn from above the liquid. The effluent gas stream contains hydrocarbon vapors. Safety engineering practices help to decrease the possibility of an explosion in such effluent gas stream. The reason for restricting the oxygen concentration of the oxidizing gas stream is a part of the safety engineering for reducing the possibility of temperature increase in the effluent gas stream attributable to vapor phase combustion of organic components.

The temperature of the reactor must be maintained within a range from about 100° C to about 175° C, and preferably about 135° C to 165° C. The cyclohexane oxidate is withdrawn as a dilute solution of cyclohexyl hydroperoxide containing from about 2% to about 12% cyclohexyl hydroperoxide based upon the content of the cyclohexane supplied by the reactor. Modifiers such as tertiary butyl alcohol, tertiary amyl alcohol, tertiary butyl hydroperoxide and/or other organic modifiers may be present in the oxidation reaction. It is important that the oxidation be conducted in the absence of a metal containing catalyst.

The feedstock for the azeotropic distillation zone can be the effluent from the oxidation reactor if the concentration of tertiary butyl alcohol in such output from the oxidation reactor contains from about 13% to about 67% tertiary butyl alcohol. It is ordinarily necessary to provide an adjustment zone between the oxidation reactor and the feedstock to the vacuum distillation zone. In the adjustment zone the concentration of the TBA is adjusted to be within the range from about 13% to about 67% tertiary butyl alcohol in the mixture of cyclohexane and tertiary butyl alcohol. The cyclohexane oxidate will contain the oxidation products including water, miscellaneous materials, cyclohexanone, cyclohexyl alcohol and the particularly desired component cyclohexyl hydroperoxide. Such oxidation products can be deemed dissolved in a solvent consisting of a mixture of 87% to 33% cyclohexane and from 13% to 67% tertiary butyl alcohol.

The vacuum distillation is conducted at a pressure within a range from about 50 millimeters to about 500 millimeters pressure. The conditions are so controlled that the amount of cyclohexane and the amount of tertiary butyl alcohol in the kettle is always such that the distillate is, throughout the entire distillation, an azeotrope of cyclohexane and tertiary butyl alcohol with or without minor components such as water. The composition of the azeotropic distillate varies in accordance with the temperature, pressure, and kettle composition.

We claim:

1. In a method for preparing a concentrated solution of cyclohexyl hydroperoxide by steps comprising oxidizing cyclohexane by liquid phase oxidation with the oxygen containing gas at a temperature in the range from 100° C. to 175° C. to provide a liquid oxidate containing from 2% to 12% cyclohexyl hydroperoxide based upon the initial cyclohexane, said oxidation being conducted in an oxidation zone at a superatmospheric pressure in the absence of a metal containing catalyst, the improvement in distillative recovery of a useful solution of cyclohexyl hydroperoxide which includes the combination of steps of:

adding sufficient tertiary butyl alcohol to said liquid oxidate to provide a feedstock containing from about 13% to 67% tertiary butyl alcohol in a mixture of cyclohexane and tertiary butyl alcohol, such amount of tertiary butyl alcohol being scheduled to provide a bottoms fraction containing tertiary butyl alcohol;

transferring said feedstock to a vacuum distillation zone;

distilling the tertiary butyl alcohol containing oxidate under vacuum at a pressure within the range from 50 to 500 mm of mercury in said vacuum distillation zone to provide throughout the entire distillation an azeotropic distillate consisting predominantly of a mixture of cyclohexane and tertiary butyl alcohol, said azeotropic distillate being recovered at a temperature lower than the temperature at which cyclohexane would be recovered at the same pressure;

and recovering a bottoms fraction containing tertiary butyl alcohol and a concentration of cyclohexyl hydroperoxide which is both greater than in said oxidate and within a range from 10% to 30% in a liquid, the loss of cyclohexyl hydroperoxide being significantly less than the distillative concentration at said pressure of cyclohexyl hydroperoxide in the absence of said azeotropic distillate consisting predominantly of a mixture of cyclohexane and tertiary butyl alcohol throughout the entire distillation.

* * * * *